(12) United States Patent
Gariépy et al.

(10) Patent No.: US 10,584,342 B2
(45) Date of Patent: *Mar. 10, 2020

(54) DNA APTAMERS SPECIFIC TO CD2000R1 AND THEIR THERAPEUTIC USES

(71) Applicant: D5PHARMA Inc., Toronto (CA)

(72) Inventors: Jean Gariépy, Toronto (CA); Reginald Gorczynski, Toronto (CA); Aaron Prodeus, Toronto (CA)

(73) Assignee: D5PHARMA Inc., Toronto, Ontario (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/948,036

(22) Filed: Apr. 9, 2018

(65) Prior Publication Data

US 2019/0085332 A1    Mar. 21, 2019

Related U.S. Application Data

(63) Continuation-in-part of application No. 15/127,909, filed as application No. PCT/CA2015/050212 on Mar. 20, 2015, now Pat. No. 9,938,533.

(60) Provisional application No. 61/968,740, filed on Mar. 21, 2014.

(51) Int. Cl.

| | |
|---|---|
| *C12N 15/115* | (2010.01) |
| *A61P 11/06* | (2006.01) |
| *A61K 47/55* | (2017.01) |
| *A61K 47/54* | (2017.01) |
| *A61K 51/04* | (2006.01) |
| *A61K 47/69* | (2017.01) |
| *A61K 47/60* | (2017.01) |

(52) U.S. Cl.
CPC .......... *C12N 15/115* (2013.01); *A61K 47/549* (2017.08); *A61K 47/55* (2017.08); *A61K 47/60* (2017.08); *A61K 47/6929* (2017.08); *A61K 51/0491* (2013.01); *A61P 11/06* (2018.01); *C12N 2310/11* (2013.01); *C12N 2310/14* (2013.01); *C12N 2310/16* (2013.01); *C12N 2310/351* (2013.01); *C12N 2310/3513* (2013.01); *C12N 2310/3515* (2013.01); *C12N 2310/3517* (2013.01)

(58) Field of Classification Search
CPC .............. C12N 15/115; A61K 47/6929; A01K 2207/05
See application file for complete search history.

(56) References Cited

U.S. PATENT DOCUMENTS

| | | | | |
|---|---|---|---|---|
| 9,938,533 B2* | 4/2018 | Gariepy | ............ | A61K 31/7088 |
| 2007/0244052 A1* | 10/2007 | Zhang | ................ | A61K 38/1709 514/21.2 |
| 2010/0104582 A1* | 4/2010 | Vignery | ............... | A61K 38/177 424/172.1 |
| 2011/0293705 A1* | 12/2011 | Irvine | .................. | A61K 9/5146 424/450 |

FOREIGN PATENT DOCUMENTS

WO    WO 2013/185241 A1    12/2013

OTHER PUBLICATIONS

Sarpong et al. Journal of Nucleic Acids vol. 2012 pp. 1-7 (Year: 2012).*
Gorczynski, Reginald M.: "CD200:CD200R-Mediated Regulation of Immunity", *International Scholarly Research Network ISRN Immunology*. vol. 2012, Article ID 682168, pp. 1-18.
Prodeus, Aaron et al.: "Agonistic CD200R1 DNA Aptamers Are Potent Immunosuppressants That Prolong Allogeneic Skin Graft Survival", *Molecular Therapy-Nucleic Acids*, (published on-line Aug. 26, 2014) 3, cl90, pp. 1-8.
International Search Report and Written Opinion issued by Canadian Patent Office, acting as the ISA, for international application PCT/CA2015/050212 dated Jun. 10, 2015.

* cited by examiner

*Primary Examiner* — Brian Whiteman

(74) *Attorney, Agent, or Firm* — McCarter & English, LLP

(57) ABSTRACT

Disclosed are short DNA aptamers that selectively recognize CD200R1, a protein expressed on the surface of myeloid and lymphoid cells that delivers immune inhibitory signals to modulate inflammation when engaged with its ligand, CD200. Also disclosed is the use of said aptamers as therapeutic agents, for the purpose of decreasing inflammatory response; treatment of spinal cord injury; treatment of an immune related disease such as arthritis, asthma, allergy, infection; as a course of treatment during or after transplantation; or for treatment of an autoimmune disorder such as systemic lupus erythematosus, Parkinson's Disease, or multiple sclerosis.

19 Claims, 14 Drawing Sheets

Specification includes a Sequence Listing.

| Name | | SEQ ID NO. |
|---|---|---|
| M21 | CCGCTACCCCATCCACGCCAATCC | SEQ ID NO.: 12 |
| M48 | GCAGATGGATGATCAGGCTATTTCC | SEQ ID NO.: 13 |
| M49 | GACGTGACATGCTTGACCAACTCGC | SEQ ID NO.: 4 |
| M52 | TTTATTACCATTATGCCTATGTAA | SEQ ID NO.: 5 |
| cApt | TCCGCATCCTCCGCCGTGCCGACC | SEQ ID NO.: 11 |

FIG. 2A

| Name | Sequence | Size (nt) | SEQ ID NO |
|---|---|---|---|
| M49 | GACGATAGCGGTGACGGCACAGACGGACGTGACATGCTTGACCAACTCGCCGTATGCCGCTTCCGTCCGTCGCTC | 75 | SEQ ID NO.: 1 |
| M49-T1 | AGCGGTGACGGCACAGACGGACGGACGTGACATGCTTGACCAACTCGCCGTATGCCGCT | 55 | SEQ ID NO.: 12 |
| M52 | GACGATAGCGGTGACGGCACAGACGTTTATTACCATTATGCCTATGTAACGTATGCCGCTTCCGTCCGTCGCTC | 74 | SEQ ID NO.: 2 |
| M52-T1 | CGGCACAGACGTTTATTACCATTATGCCTATGTAACGTATGCCG | 44 | SEQ ID NO.: 13 |
| M52-T2 | ACGTTTATTACCATTATGCCTATGTAACG | 29 | SEQ ID NO.: 14 |

FIG. 2C

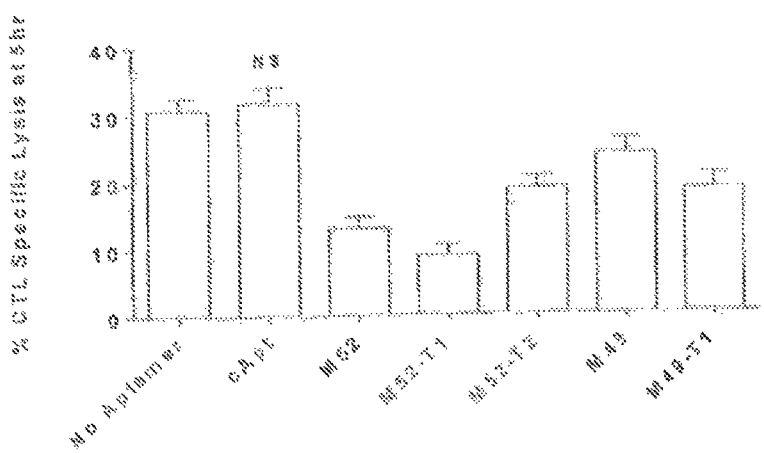

FIG. 8A
| | | |
|---|---|---|
| | | SEQ ID NO. 7 |
| CCS.8 | CCCCTCCGAGTGATATGTAATCCTA | SEQ ID NO. 15 |
| CCS.13 | CACCGCTCTTATGCCACCATTTTCA | SEQ ID NO. 6 |
FIG. 8B
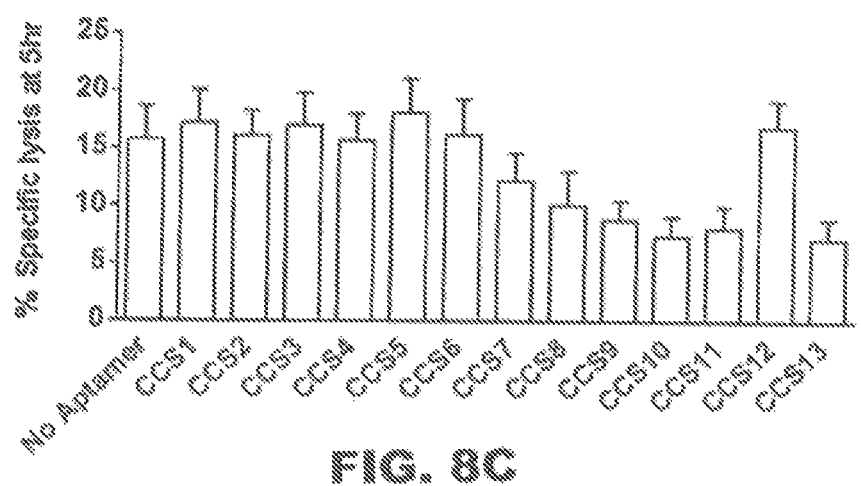
FIG. 8C
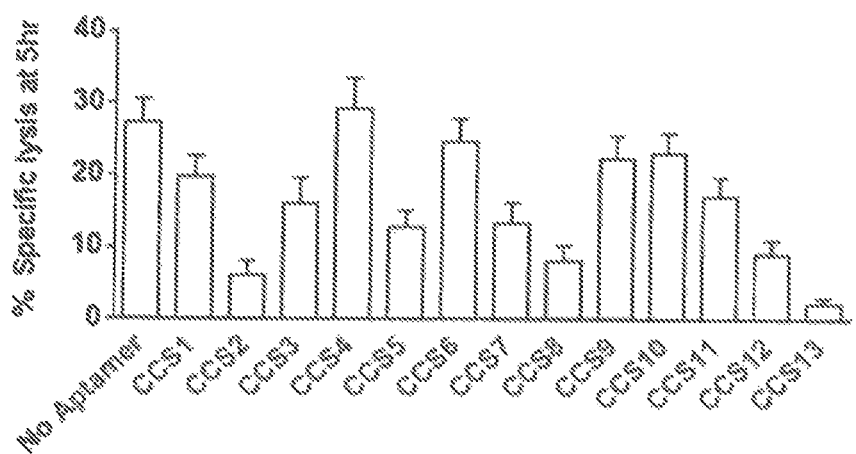

SEQUENCE LISTING

```
<160> NUMBER OF SEQ ID NOS: 16

<210> SEQ ID NO 1
<211> LENGTH: 75
<212> TYPE: DNA
<213> ORGANISM: Artificial Sequence
<220> FEATURE:
<223> OTHER INFORMATION: Aptamer

<400> SEQUENCE: 1
gacgatagcg gtgacggcac agacggacgt gacatgcttg accaactcgc cgtatgccgc      60
ttccgtccgt cgctc                                                      75

<210> SEQ ID NO 2
<211> LENGTH: 74
<212> TYPE: DNA
<213> ORGANISM: Artificial Sequence
<220> FEATURE:
<223> OTHER INFORMATION: Aptamer

<400> SEQUENCE: 2
gacgatagcg gtgacggcac agacgtttat taccattatg cctatgtaac gtatgccgct      60
tccgtccgtc gctc                                                       74

<210> SEQ ID NO 3
<211> LENGTH: 75
```

```
<212> TYPE: DNA
<213> ORGANISM: Artificial Sequence
<220> FEATURE:
<223> OTHER INFORMATION: Aptamer

<400> SEQUENCE: 3
gacgatagcg gtgacggcac agacgcaccg ctcttatgcc accatttcca cgtatgccgc    60
ttccgtccgt cgctc                                                    75

<210> SEQ ID NO 4
<211> LENGTH: 25
<212> TYPE: DNA
<213> ORGANISM: Artificial Sequence
<220> FEATURE:
<223> OTHER INFORMATION: Aptamer

<400> SEQUENCE: 4
gacgtgacat gcttgaccaa ctcgc                                         25

<210> SEQ ID NO 5
<211> LENGTH: 24
<212> TYPE: DNA
<213> ORGANISM: Artificial Sequence
<220> FEATURE:
<223> OTHER INFORMATION: Aptamer

<400> SEQUENCE: 5
tttattacca ttatgcctat gtaa                                          24

<210> SEQ ID NO 6
<211> LENGTH: 25
<212> TYPE: DNA
<213> ORGANISM: Artificial Sequence
<220> FEATURE:
<223> OTHER INFORMATION: Aptamer

<400> SEQUENCE: 6
caccgctctt atgccaccat tttca                                         25

<210> SEQ ID NO 7
<211> LENGTH: 75
<212> TYPE: DNA
<213> ORGANISM: Artificial Sequence
<220> FEATURE:
<223> OTHER INFORMATION: library
<220> FEATURE:
<221> NAME/KEY: misc_feature
<222> LOCATION: (26)..(50)
<223> OTHER INFORMATION: n can be any base; this is a random synthetic
      oligonucleotide library.

<400> SEQUENCE: 7
gacgatagcg gtgacggcac agacgnnnnn nnnnnnnnnn nnnnnnnnnn cgtatgccgc    60
ttccgtccgt cgctc                                                    75

<210> SEQ ID NO 8
<211> LENGTH: 25
<212> TYPE: DNA
<213> ORGANISM: artificial sequence
<220> FEATURE:
<223> OTHER INFORMATION: primer

<400> SEQUENCE: 8
gacgatagcg gtgacggcac agacg                                         25
```

```
<210> SEQ ID NO 9
<211> LENGTH: 25
<212> TYPE: DNA
<213> ORGANISM: artificial sequence
<220> FEATURE:
<223> OTHER INFORMATION: primer

<400> SEQUENCE: 9
gagcgacgga cggaagcggc atacg                                          25

<210> SEQ ID NO 10
<211> LENGTH: 75
<212> TYPE: DNA
<213> ORGANISM: artificial sequence
<220> FEATURE:
<223> OTHER INFORMATION: Aptamer

<400> SEQUENCE: 10
gacgatagcg gtgacggcac agacgtcccg catcctccgc cgtgccgacc cgtatgccgc    60
ttccgtccgt cgctc                                                     75

<210> SEQ ID NO 11
<211> LENGTH: 25
<212> TYPE: DNA
<213> ORGANISM: Artificial Sequence
<220> FEATURE:
<223> OTHER INFORMATION: Aptamer

<400> SEQUENCE: 11
tcccgcatcc tccgccgtgc cgacc                                          25

<210> SEQ ID NO 12
<211> LENGTH: 59
<212> TYPE: DNA
<213> ORGANISM: Artificial Sequence
<220> FEATURE:
<223> OTHER INFORMATION: Aptamer

<400> SEQUENCE: 12
agcggtgacg gcacagacgg acggacgtga catgcttgac caactcgccg tatgccgct     59

<210> SEQ ID NO 13
<211> LENGTH: 44
<212> TYPE: DNA
<213> ORGANISM: Artificial Sequence
<220> FEATURE:
<223> OTHER INFORMATION: Aptamer

<400> SEQUENCE: 13
cggcacagac gtttattacc attatgccta tgtaacgtat gccg                     44

<210> SEQ ID NO 14
<211> LENGTH: 29
<212> TYPE: DNA
<213> ORGANISM: Artificial Sequence
<220> FEATURE:
<223> OTHER INFORMATION: Aptamer

<400> SEQUENCE: 14
acgtttatta ccattatgcc tatgtaacg                                      29

<210> SEQ ID NO 15
<211> LENGTH: 25
<212> TYPE: DNA
<213> ORGANISM: Artificial Sequence
<220> FEATURE:
```

-continued

```
<223> OTHER INFORMATION: Aptamer

<400> SEQUENCE: 15
cccctccgag tgatatgtaa tccta                                              25

<210> SEQ ID NO 16
<211> LENGTH: 75
<212> TYPE: DNA
<213> ORGANISM: Artificial Sequence
<220> FEATURE:
<223> OTHER INFORMATION: Aptamer

<400> SEQUENCE: 16
gacgatagcg gtgacggcac agacgcccct ccgagtgata tgtaatccta cgtatgccgc        60
ttccgtccgt cgctc                                                         75
```

DNA APTAMERS SPECIFIC TO CD2000R1 AND THEIR THERAPEUTIC USES

CROSS-REFERENCE TO RELATED APPLICATIONS

This application is a continuation-in-part of U.S. patent application Ser. No. 15/127,909, filed on Sep. 21, 2016, which is a 35 U.S.C. § 371 national stage filing of International Application No. PCT/CA2015/050212, filed on Mar. 20, 2015, which claims the benefit of priority of U.S. Provisional Application No. 61/968,740, filed on Mar. 21, 2014. The contents of each of the foregoing applications are incorporated herein by reference in their entirety.

BACKGROUND OF THE INVENTION

This invention relates to the discovery and uses of a class of short DNA aptamers that selectively recognize CD200R1, a protein expressed on the surface of myeloid and lymphoid cells that delivers immune inhibitory signals to modulate inflammation when engaged with its ligand, CD200.

CD200R1

CD200R1 is a type I glycoprotein expressed on cells of myeloid and lymphoid lineage. It delivers immune inhibitory signals upon ligation to the widely distributed cell surface glycoprotein CD200. Structurally, CD200R1 contains two Ig-like domains, a transmembrane region, and a cytoplasmic tail containing a NXPY motif which is phosphorylated upon CD200 ligation inducing recruitment of the adaptor protein Dok2 and subsequent signal transduction.

The physiological importance of CD200:CD200R1 inhibitory signalling has been established in a number of diseases including arthritis, transplantation, and a number of central nervous system autoimmune diseases such as Parkinson's disease (PD) and multiple sclerosis (MS). For instance, a recombinant CD200.Fc fusion protein has been shown to behave as a potent in-vivo immunosuppressant, prolonging allo- and xenograph survival as well as suppressing collagen-induced arthritis in mice. Also, the inhibition of CD200:CD200R1 signalling on microglial cells using a blocking antibody to CD200R1 exacerbated neurodegeneration and disease state in a murine model of experimental autoimmune encephalomyelitis (EAE). These findings were further supported in a separate EAE study where treatment with CD200.Fc suppressed microglial accumulation, and decreased the production of pro-inflammatory cytokines IL-6, TNF-α, and nitric oxide by myeloid cells in the spleen and central nervous system.

CD200R1 signalling has also been implicated in tissue specific autoimmunity, as both systemic and local treatment with an anti-CD200R1 agonistic antibody suppressed experimental autoimmune uveitis (EAU), a model of $CD4^+$ T-cell organ-specific autoimmunity of the eye.

Thus the development of safe and effective immunomodulatory agents which stimulate CD200R1 signalling are of clinical interest. Despite advances in antibody and protein engineering, the major drawbacks of protein-based CD200R1 stimulators are their immunogenicity arising from their chronic use and their production costs resulting in expensive therapies for patients.

It would be useful to have a non-protein composition that binds to CD200R1 with high specificity and/or affinity without immune responses. Such a composition may act as a stimulator of immune inhibitory signalling by selectively binding, and hindering the function of, or inactivating, the CD200R1, and thus be useful as a treatment for immune related disease such as arthritis, asthma, allergy, infection, as a course of treatment during or after transplantation, or for treatment of autoimmune disorders such as systemic lupus erythematosus, Parkinson's Disease, or multiple sclerosis. Such a composition may also be useful conjugated or otherwise associated with a cytotoxic agent for specifically targeting such an agent to a CD200R1 expressing or over-expressing cell.

Aptamers

Aptamers are short, single-stranded nucleic acid oligomers (ssDNA or RNA) which adopt a specific tertiary structure allowing them to bind to molecular targets with high specificity and affinities comparable to that of monoclonal antibodies, through interactions other than classic Watson-Crick base pairing. In some cases, aptamers will display functional properties beyond just binding to their target. For instance, an aptamer to the inflammation factor human neutrophil elastase (hNE) was shown to significantly reduce lung inflammation in rats and displayed greater specificity for their target than an antielastase IgG control. Examples of other aptamers exhibiting functional attributes include a DNA aptamer to anti-HIV reverse transcriptase and RNA aptamers to the basic fibroblast growth factor and vascular endothelial growth factor. Finally, a single-stranded DNA aptamer selected to bind to thrombin has been shown to inhibit thrombin-catalyzed fibrin-clot formation in vitro using either purified fibrinogen or human plasma. Thus, aptamers can be derived to either block protein-protein interactions or act as agonists to cell surface receptors.

Aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets. They have several advantages over antibodies. As a class, they have demonstrated therapeutically acceptable toxicity, and a lack of immunogenicity. Aptamers can typically be administered by subcutaneous injection due to their low solubility as compared to antibodies. Aptamers are chemically robust, and can be readily manufactured since they can be chemically synthesized.

In contrast to antibodies and other protein-based agents, aptamers have a number of advantages including a long shelf life, low immunogenicity, and chemical synthesis. However, aptamers as therapeutic entities do display poor pharmacokinetic profiles as unprotected RNA or DNA aptamers are rapidly removed from circulation due to renal filtration and nuclease degradation. However, improved pharmacokinetic properties have been observed upon site-specific conjugation of polyethylene glycol (PEG) polymers to aptamer termini as well as the incorporation of nuclease resistant 2'-F or 2'-Me nucleotides in the case of RNA aptamers. Functional aptamers which target co-stimulatory or co-inhibitory receptors represent a new class of targeted immunotherapeutic agents with unique and advantageous properties. Thus far, aptamers with either agonistic or antagonistic function have been developed to a number of immune co-receptors including CTLA-4, 4-1BB, OX-40, IL-6R, IL-10R, and CD28. However, only a few of them have been validated for activity in-vivo.

Membrane impermeant aptamers have the potential to be used as antagonists themselves, or to serve as intracellular delivery agents specific to an internalized surface marker on a cancer cell, for example. Therapeutic cargos such as siRNAs, antisense oligonucleotides, ribozymes as well as low MW drugs, can be directly coupled to aptamers or packaged into particles modified with aptamers. Aptamer-containing conjugates can be constructed by chemically coupling a drug, such as a chemotherapeutic drug, to the aptamer via a linker or by intercalating the drug into the aptamer folded structure creating a physical complex. The cargo is then imported into a target cell due to the aptamer specificity while reducing toxicity towards other cells. Cargos can be conjugated to aptamers during solid-phase synthesis or post-synthesis by incorporating an amino or thiol group at one end of the oligonucleotide during its assembly. A therapeutic protein can also be coupled to the aptamer, to reach an intracellular substrate target. Aptamers can also be conjugated to radionuclides or metal chelators to image or kill cells targeted by the aptamer. Recently, aptamers have been conjugated to nanostructures, representing a promising class of new agents for targeted imaging and therapy. Thus, cargos can also be encapsulated into such nanopaticles decorated on their surface with aptamers. The targeted structures include nanorods, quantum dots as well as soft and hard nanoparticles.

An aptamer that binds with high specificity and/or affinity to CD200R1 would be desirable for its potential as a simple (compared, for example, to an antibody), synthetic, potentially non-immunogenic stimulator of immune inhibitory signalling. Such a compound would be useful for a variety of research, diagnostic, and therapeutic uses, for example, for imaging, diagnosis, or for the treatment of immune related disease such as arthritis, allergy, asthma, infection, as a course of treatment during or after transplantation, or for treatment of autoimmune disorders such as systemic lupus erythematosus, Parkinson's Disease. or multiple sclerosis. Such a compound could also be useful conjugated or otherwise associated with a cytotoxic agent for specifically targeting such an agent to a CD200R1-expressing or over-expressing cell.

Asthma

Asthma is a common long-term inflammatory disease of the airways of the lungs, affecting hundreds of millions of individuals, and causing hundreds of thousands of deaths each year. Symptoms of asthma include episodes of coughing, shortness of breath, wheezing, coughing, and difficulty breathing. Currently, the most common treatment for asthma is inhaled or intranasally administered corticosteroids. They may be combined with long-acting beta agonists, or anti-leukotriene agents. Effectiveness of these treatments is highly variable. The cause of asthma is also highly variable, and may include both environmental factors and genetic factors. Many of the genes associated or implicated with asthma are related to the immune system, or modulating inflammation.

BRIEF DESCRIPTION OF THE FIGURES

FIG. 1A: Aptamer sequences which were identified after 15 iterative SELEX rounds. Full length aptamers consist of an internal variable region of 25 bp, flanked by two constant regions of 25 bp each. Control aptamer (cApt) has a scrambled variable sequence with the same constant regions and was used throughout this study. FIG. 1B: DNA aptamers were added to 5 day allogeneic-MLC with $2.5 \times 10^5$ C57BL/6 responder cells and an equal number of irradiated BALB/c stimulator cells. CTLs were assayed by $^{51}$Cr release of loaded P815 mastocytoma target cells in 5 hours at a 25:1 effector-to-target ratio. Soluble CD200Fc was used as a positive control. Each bar represents average CTL specific lysis±SEM (n=4). Aptamers were added at 22.5 µg/mL (black), 7.5 µg/mL (grey) or 2.5 µg/mL (white). *P<0.01 compared to cApt or no treatment. s\Shown is a representative of three independent experiments.

FIGS. 2A, 2B, and 2C show Guided Truncation of CD200R1 aptamers M49 and M52. FIG. 2A: Shown are name, sequence and length of truncated aptamers. Bolded, underlined sequences represent the constant primer regions on each sequence. FIG. 2B: Aptamer sequences were truncated on the basis of secondary structure predictions. The secondary structure prediction on the left is of the M49 aptamer (SEQ ID NO: 1), and the secondary structure prediction on the right is of the M52 aptamer (SEQ ID NO: 2). The M49-T1 (SEQ ID NQ-L 2 M52-T1 (SEQ ID NO: 13), and M52-T2 (SEQ ID NO: 14) aptamer sequence truncations are indicated by the respective bars crossing SEQ ID NO: 1 (for M49-T1) and SEQ ID NO: 2 (for M52-T1 and M52-T2) s shown. FIG. 2C: Truncated aptamers were added to 5 day allogenic-MLC with an equal number of responder C57BL/6 splenocytes and irradiated BALC/c stimulator cells. CTLs were assayed by monitoring $^{51}$Cr release from P815 mastocytoma target cells incubated for 5 hours in a 25:1 effector to target culture. Truncated sequences M52-T1 and M49-T1 suppress CTL induction with efficacy equivalent to full length aptamers. Samples were tested in triplicate and shown is mean±SEM (*P<0.01, NS=not significant). Graph is a representative from 3 independent experiments.

FIG. 3A: DNA aptamers were synthesized with a 5' amine with a C6 spacer and reacted with an excess of monofunctional NHS-PEG overnight. FIG. 3B: FPLC size exclusion chromatography using a Superdex75 column was used to purify the crude reaction (top) to yield purified full length PEGylated aptamers (bottom). Absorbance (UV260 nm) was used to track elution of free nucleic acid and nucleic acid conjugates. The first peak at 7.93 mL corresponds to PEG-Aptamer, and 9.66 mL peak corresponds to unreacted aptamer. FIG. 3C: Free aptamer (1), crude PEG-aptamer reaction mix (2), and FPLC purified PEG-aptamer (3) were run on an 8% polyacrylamide gel and visualised by silver stain to detect nucleic acids.

FIG. 4A: PEGylated and non-PEGylated aptamers (7.5 g/mL nucleic acid) were added to 5 day allogeneic-MLC of C57BL/6 responder cells with an equal number of irradiated BALB/c stimulator cells and CTL induction monitored by measuring P815 mastocytoma lysis. PEG-M49 and PEG-M52 suppress CTL induction by ~60%. Each bar represents mean±SEM. *P<0.01 relative to no treatment, NS=not significant. FIG. 4B: To monitor aptamer induced phosphorylation of the CD200R1 cytoplasmic tail, HEK293 cells transfected to express CD200R1 were incubated for 30 minutes with PEG-M49 or PEG-M52. FIG. 4C: Cells were lysed and CD200R1 immunoprecipitated and run on a western blot developed with an antibody specific to phosphorylated-CD200R1 cytoplasmic tail. Supernatant from a CD200 expressing cell was used as a positive control. (+) indicates addition of 5 uM PEG-M49, PEG-M52, or CD200+ supernatant, whereas (−) indicates media only. Shown is a representative of two independent experiments.

FIG. 5A: Experimental outline of in-vivo experiments. C57BL/6 mice were treated over 12 days with intravenous tail vein injections of 151 µg PEG-M49, PEG-M52, PEG-cApt, or CD200Fc (positive control) in 72 intervals with low-dose 0.5 mg/kg rapamycin. FIG. 5B: After 14 days mice were sacrificed and splenocytes used as responder cells in 5 day allogeneic MLC assays during which the treatment molecule was (white) or was not (grey) added in culture. In-vivo administration of PEG-M49 and PEG-M52 in combination with rapamycin suppressed CTL induction without further addition of aptamer in culture (P<0.01). Shown is a representative of two independent experiments.

FIG. 6A: Experimental outline of experiment. C57BL/6 mice (n=6) received BALB/c skin allografts on day 0 and were treated in 72 hr intervals with PBS (control) or 15 μg PEG-cApt, PEG-M49. PEG-M52 or CD200Fc (positive controls) in combination with low dose (0.5 mg/kg) rapamycin. Injections were given intravenously and graft survival monitored by a blinded investigator. FIG. 6B: Treatment with PEG-M49 and PEG-M52 significantly extended graft survival (P<0.05, Mantel-Cox Test) relative to control. Arrow represents the time of last treatment (day 15). Shown is a representative of two independent experiments.

FIGS. 8A, 8B, and 8C show Cross Species Anti-CD200R Aptamers Identified by SELEX. FIG. 8A: At cycle 15 enriched SELEX pools towards both human and murine CD200R recombinant proteins were sequenced using Ion-Torrent Next-Generation Sequencing. Thirteen sequences were identified to be enriched in both pools and labelled CCS1-13 accordingly (CD200R1 cross species). FIGS. 8B and 8C: Each aptamer was tested for suppression of CTL induction in both human (FIG. 8B) and mouse (FIG. 8C) 5 day allogenic mixed leukocyte cultures (MLC). Aptamers were added to MLC at 10 uM. CTLs were identified by monitoring $^{51}$Cr release from loaded target cells at a 30:1 effector to target ratio. CCS.13 showed at least 50% suppression of CTL induction in both human and mouse allogenic cultures and was chosen for further evaluation.

FIG. 10A: Experimental outline of in-vivo experiment. C57BL/6 mice were treated over 12 days with intravenous tail vein injections of 15 μg PEG-CCS.13. PEG-cApt, or CD200Fc (positive control) and low dose (0.5 mg/kg) in 72 intervals. After 14 days mice were sacrificed and splenocytes used as responder cells in 5 day allogeneic MLC assays. As shown in FIG. 10B, in-vivo administration of PEG-CCS.13 in combination with rapamycin suppressed CTL induction without further addition of aptamer in culture (*P<0.01), whereas rapamycin alone or with PEG-cApt did not (NS=not significant).

FIG. 11A: Experimental outline of experiment. C57BL/6 mice (n==6) received BALB/c skin allografts on day 0 and were treated in 72 hr intervals with PBS (control) or 15 μg PEG-cApt, PEG-M49, PEG-M52 or CD200Fc in combination with low dose (0.5 mg/kg) rapamycin. Injections were given intravenously and graft survival monitored by a blinded investigator. FIG. 11B: Treatment with PEG-CCS.13 in combination with rapamycin significantly extended graft survival (P<0.05, Mantel-Cox Test) relative to PBS, or PEG-cApt with rapamycin. Arrow represents the time of last treatment (day 15).

DETAILED DESCRIPTION

Figures 1A, 1B:
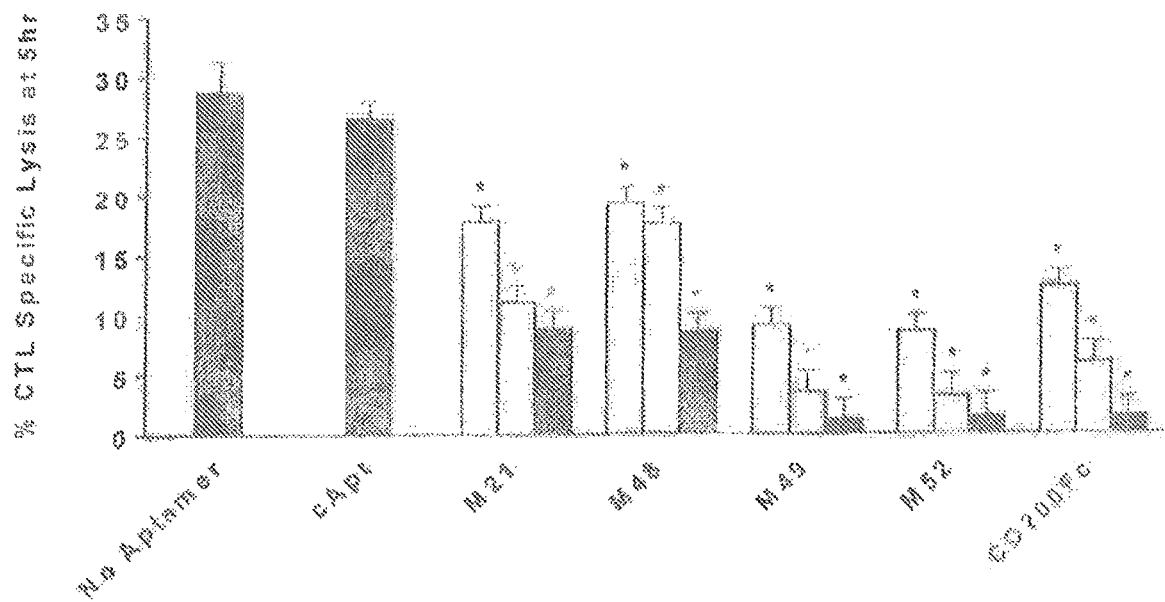
FIGS. 1A and 1B show that DNA Aptamers selected to bind to the extracellular domain of murine CD200R1 suppress CTL induction in primary MLC.

Disclosed are a series of aptamers which bind to murine CD200R1 and stimulate immune inhibitory signalling. These agonistic aptamers (termed, herein, M49, M52, and CCS13) exhibit in vitro immunosuppressive properties as measured by suppression of cytotoxic T-lymphocyte (CTL) induction in allogenic-mixed lymphocyte cultures (allo-MLC). Importantly, PEGylated conjugates of these aptamers retain bioactivity in-vitro and function as potent immunosuppressants when administered in-vivo. The therapeutic potential of agonistic CD200R1 aptamers is demonstrated—intravenous administration of PEG-M49 and PEG-M52 prolongs the survival of murine skin allografts to a similar extent as CD200.Fc. CCS13 was also shown to be a cross-species aptamer, having function in both humans and mice. The aptamers showed to suppress CTL induction in 5 day mixed leukocyte culture (MLC) and cause rapid phosphorylation of the CD200R1 cytoplasmic tail thereby initiating immune inhibitory signalling. PEGylated forms of these aptamers were synthesized and show significant in-vivo immunosuppression. In a murine model of transplantation, intravenous injection of PEGylated aptamers enhanced survival of allogeneic skin grafts as effectively as a soluble CD200Fc. As DNA aptamers exhibit inherent advantages over conventional protein-based therapeutics including low immunogenicity, ease of synthesis, low cost, and long shelf life, the disclosed CD200R1 specific DNA aptamers are a useful and safe non-steroidal anti-inflammatory therapeutic agent.

CD200R11 aptamers are disclosed at Table 1 (M49, M52, CCS8 and CCS13, having as their nucleotide sequences SEQ ID NOs 1, 2, 16 and 3, respectively); all show high specificity and binding affinity to CD200R1, and in two cases (CCS8 and CCS13) has been shown capable of cross-species agonistic activity. The CD200R1-specific regions of these aptamers are shown herein at Table 2, (TM49, TM52, TCCS8 and TCCS13), having as their nucleotide sequences the SEQ ID NOs.: 4, 5, 15 and 6, respectively.

TABLE 1

CD200R1 specific DNA aptamers

M49:

GACGATAGCGGTGACGGCACAGACGGACGTGACATGCTTGACCAACTCGC
CGTATGCCGCTTCCGTCCGTCGCTC (SEQ ID NO.: 1)

M52:

GACGATAGCGGTGACGGCACAGACGTTTATTACCATTATGCCTATGTAAC
GTATGCCGCTTCCGTCCGTCGCTC (SEQ ID NO.: 2)

CCS8:

GACGATAGCGGTGACGGCACAGACGCCCCTCCGAGTGATATGTAATCCTA
CGTATGCCGCTTCCGTCCGTCGCTC (SEQ ID NO: 16)

CCS13:

GACGATAGCGGTGACGGCACAGACGCACCGCTCTTATGCCACCATTTTCA
CGTATGCCGCTTCCGTCCGTCGCTC (SEQ ID NO.: 3)

TABLE 2

| CD200R1 - specific regions of the CD200R1 aptamers | |
|---|---|
| TM49: | GACGTGACATGCTTGACCAACTCGC (SEQ ID NO.: 4) |
| TM52: | TTTATTACCATTATGCCTATGTAA (SEQ ID NO.: 5) |
| TCCS8: | CCCCTCCGAGTGATATGTAATCCTA (SEQ ID NO.: 15) |
| TCCS13: | CACCGCTCTTATGCCACCATTTTCA (SEQ ID NO.: 6) |

Example 1: Aptamer Selection ssDNA aptamers specific towards murine CD200R1 were identified using the PCR-based Systematic Evolution of Ligands by Exponential Enrichment (SELEX) method (Ellington and Szostak, Nature, 1990 Aug. 30:346(6286):818-22; Tuerk and Gold, Science 1990 Aug. 3 249(4968):505-10; Bock et al., Nature 1992 Feb. 6:355(6360):564-6, all incorporated herein by reference). A 25 nucleotide long random synthetic oligonucleotide library flanked by 25-base long 5' and 3' primer regions (5'-G ACGATAGCGGTGACG-GCACAGACGNNNNNNNNNNNNNNNNNNNNNNNNN NNCGTATGCCGCTTCCGTCCGTCGCTC-3', SEQ ID NO.: 7) was synthesized by Integrated DNA Technologies (IDT) along with the corresponding primer sequences (Forward 5'-GACGATAGCGGTGACGGCACAGACG-3' (SEQ ID NO.: 8) and Reverse 5' GAGCGACGGACGGAAGCG-GCATACG-3' (SEQ ID NO.: 9)). A 4 nmol aliquot of the library representing ~$2.5 \times 10^{15}$ sequences was adsorbed onto MagneHis Ni-Particles (Promega) at 37° C. for 1 hr to remove sequences which bound to the solid support. The resulting sub-library was incubated for 1 hr at 37° C. with 10 µg of a recombinant HIS-tagged murine CD200R1 protein immobilized on MagneHis Ni-Particles suspended in 1 mL phosphate buffered saline (PBS, pH 7.4). Unbound and weakly bound sequences were removed by washing the beads with PBS for 5 minutes and protein-aptamer complexes were eluted with PBS containing 0.5M imidazole. Aptamers were recovered using the Qiagen Nucleotide Removal kit following manufacturer's recommendations and the ssDNA pool was amplified for the next round of selection using asymmetric PCR at a 10:1 forward:reverse primer ratio. Fifteen rounds of selection were performed with the selection stringency increasing as the concentration of CD200R1 was halved every three rounds while simultaneously increasing the number of wash steps. After the $15^{th}$ cycle, selected DNA aptamers were cloned into pCR4-TOPO vector (Life Technologies) and sequenced.

Over 20 DNA aptamer sequences specifically recognizing a murine CD200R1 recombinant protein were identified after 15 rounds of SELEX screens. These 75-base long sequences along with a scrambled control aptamer (cApt) (GACGATAGCGGTGACGGCACAGACGTCCCGCATC-CTCCGCCGTCCCGACCCGTATG CCGCTTCCGTC-CGTCGCTC (SEQ ID NO.: 10), containing specific region TCCCGCATCCTCCGCCGTGCCGACC (SEQ ID NO.: 11)) were synthesized and systematically screened for CD200R1 agonistic activity by evaluating their capability to suppress the induction of cytotoxic T-lymphocyte (CTL) in 5 day allo-mixed lymphocyte cultures. Aptamer-induced suppression of CTL induction was monitored using a chromium release assay of labeled P815 mastocytoma serving as target cells for CTL lysis. Four aptamers M21, M48, M49, and M52 (FIG. 1A) displayed CD200R1 agonistic properties (FIG. 1B). Specifically aptamers M49 and M52 suppressed CTL induction at levels comparable to the soluble CD200Fc ligand with less than 5% CTL specific lysis of P815 cells occurring at aptamer concentrations ≥7.5 µg/mL. M49 and M52 were chosen for further evaluation.

Figure 2B:
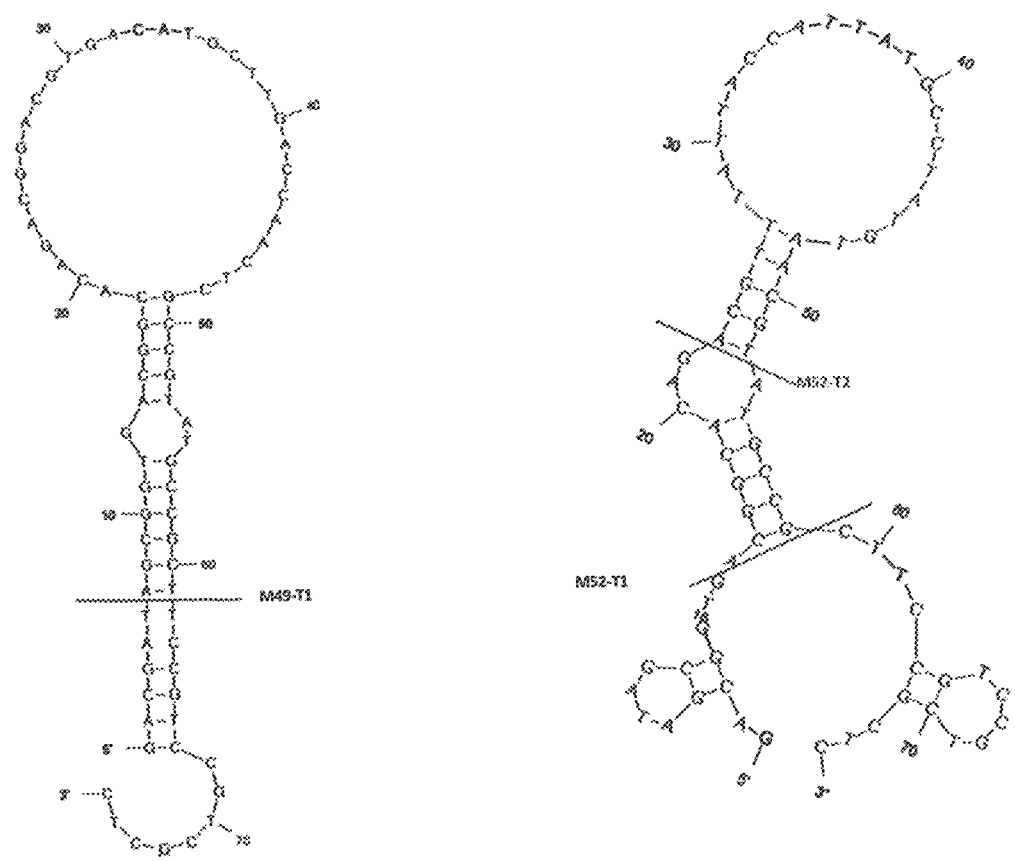

The 75-base long M49 and M52 aptamer sequences were further truncated based on their predicted secondary structure derived from mfold software (FIGS. 2A and 2B). M49 retained agonistic activity when truncated to a minimal size of 55-bases TrM49 (SEQ ID NO.: 12) while the optimal activity for M52 was retained down to a length of 44 bases TrM52 (SEQ ID NO.: 13) (FIG. 2C).

Example 2: Allogeneic Mouse Mixed Lymphocyte Culture (Allo-MLC)

Agonistic CD200R1 aptamers were identified and evaluated for their ability to suppress cytotoxic T-lymphocyte (CTL) induction in 5 day allo-MLC. Briefly, $2.5 \times 10^5$ C57BL/6 responder splenocytes were incubated with an equal number of irradiated BALB/c stimulator cells in the presence of synthetic aptamers, PEGylated aptamers, or CD200Fc for 5 days. CTL induction was assayed by monitoring the release of $^{51}Cr$ from loaded P815 mastocytoma target cells over a 5 hour time period at a 25:1 effector-to-target ratio.

Example 3: PEGylation of DNA Aptamers

Figure 3A:
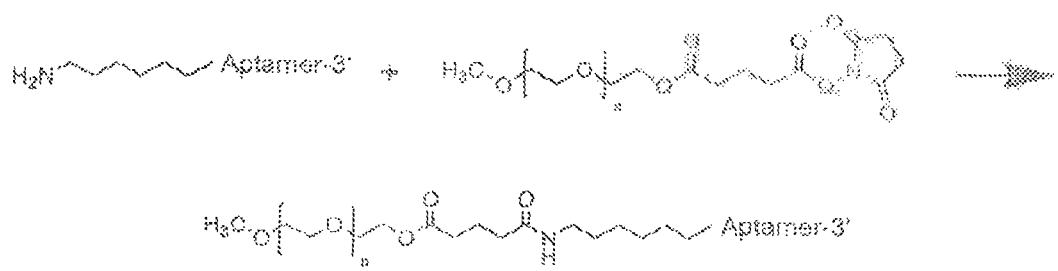
FIGS. 3A, 3B, and 3C show Modification and Purification of DNA aptamers with a 20 kDa PEG.
Figure 3B:
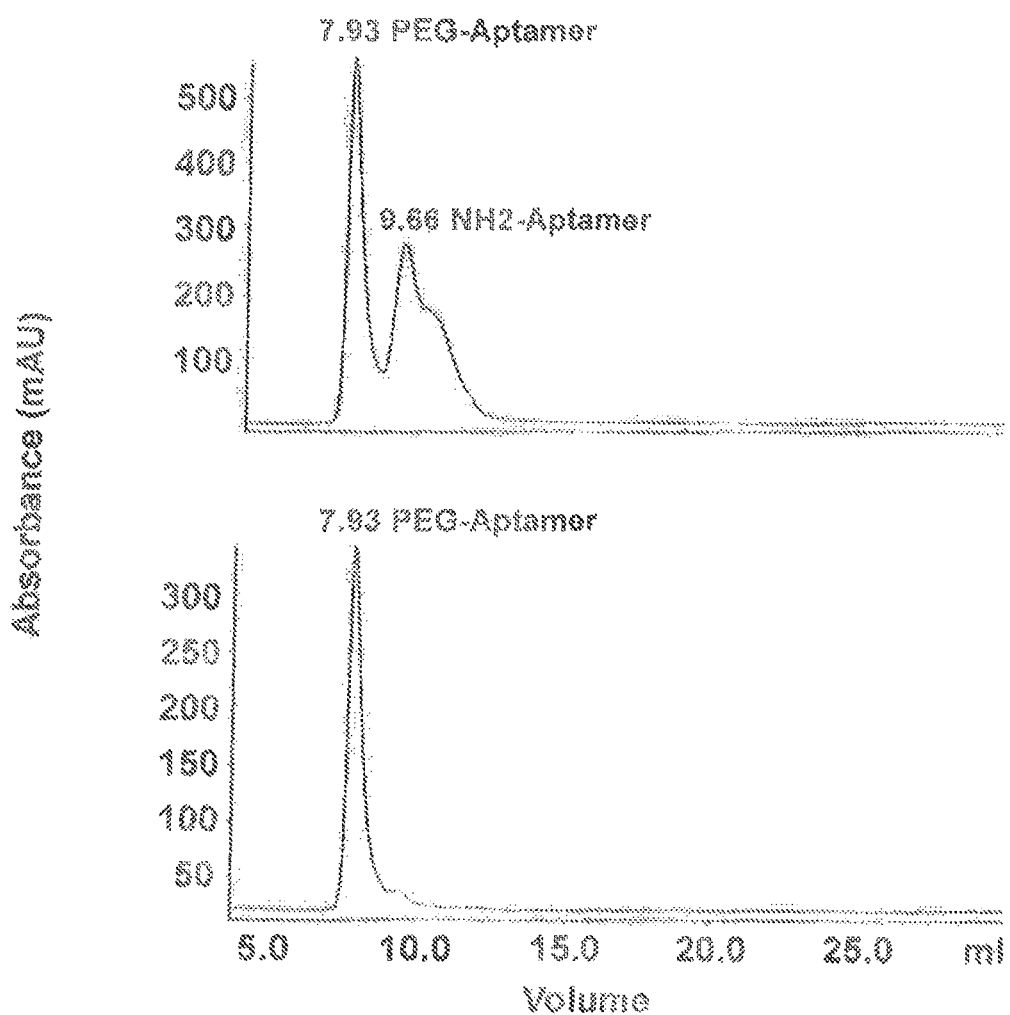
Figure 3C:
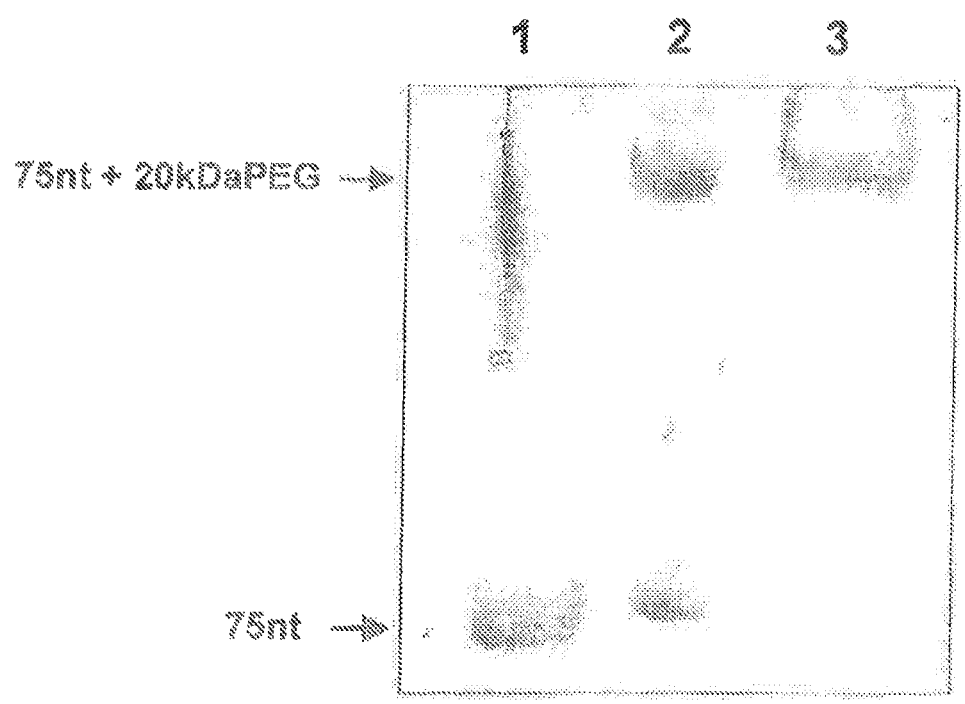

The 5' termini of aptamer M49 (SEQ ID NO.: 4), M52 (SEQ ID NO.: 5), and the control aptamer cApt (SEQ ID NO.: 10) were modified with a 20 kDa polyethylene glycol (PEG) moiety to increase their circulatory half-life, as shown schematically in FIG. 3A. Briefly, a 5' amino group with a hexylamine arm was incorporated into each DNA aptamer during synthesis (IDT). A 100-molar excess of mPEG-succinimidyl glutarate ester powder (Creative PEG-Works, Winston Salem, N.C., USA) was added stepwise over a period of 10 hours to 25 µM solutions of the modified aptamers dissolved in 100 mM $NaHCO_3/CH_3CN$ (1:1 pH 8.5). The PEGylated aptamers were purified by ultrafiltration using Amicon Ultra Centrifugal Filters with a 30 kDa MWCO (Millipore) and size exclusion fast protein liquid chromatography (FPLC) using a Superdex 75 10/300 column (GE Healthcare) with 100 mM $NH_4CO_3$ as eluent. Purified PEGylated-aptamer conjugates were lyophilized and resuspended in sterile PBS for subsequent experiments. Purity of the final PEGylated products were confirmed by size exclusion FPLC (FIG. 3B) and polyacrylamide gel electrophoresis (FIG. 3C).

Figure 4A:
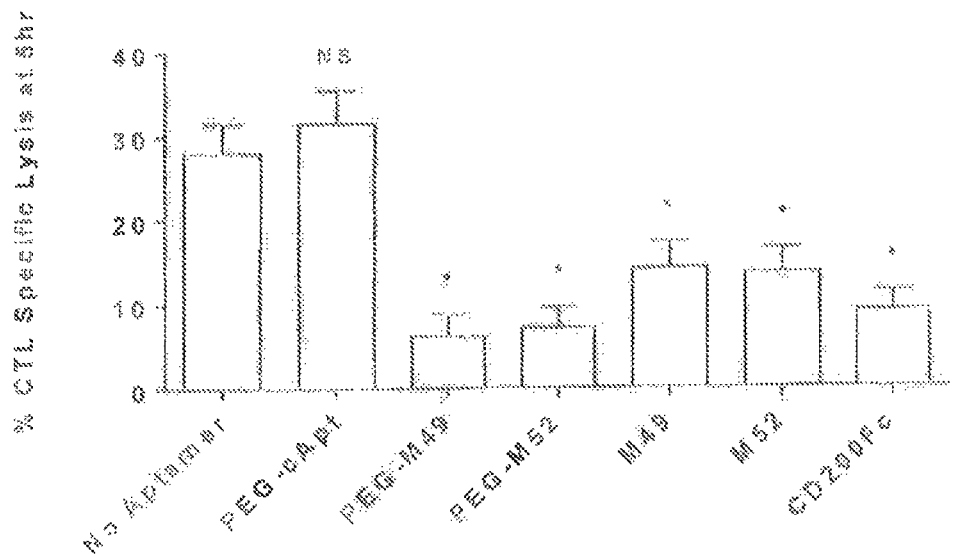
FIGS. 4A, 4B, and 4C show PEG conjugated M49 and M52 function act as CD200R1 agonists.
Figure 4B:
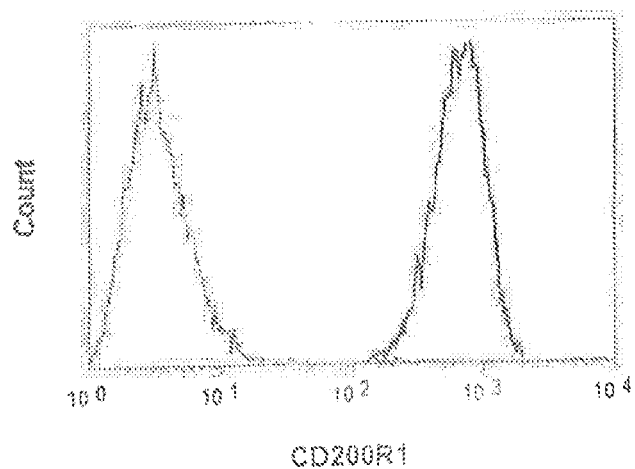
Figure 4C:
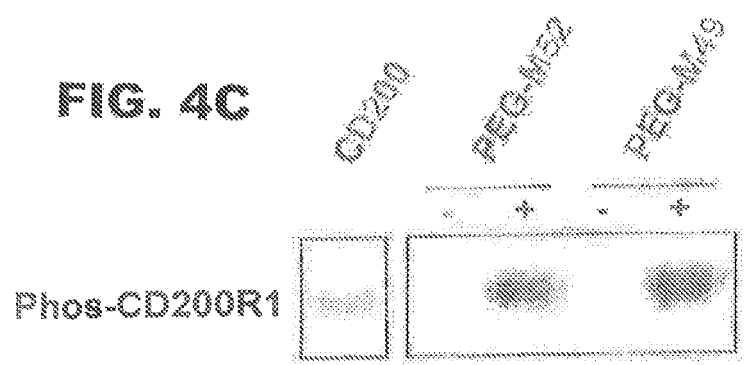
Figure 5A:
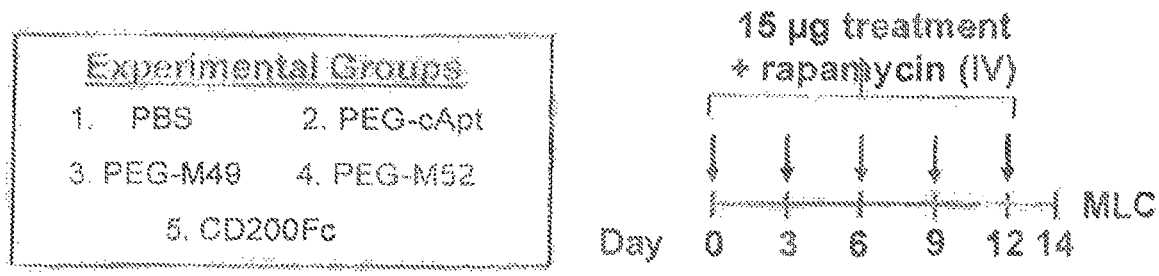
FIGS. 5A and 5B show PEG-M49 and PEG-M52 function in-vivo.
Figure 5B:
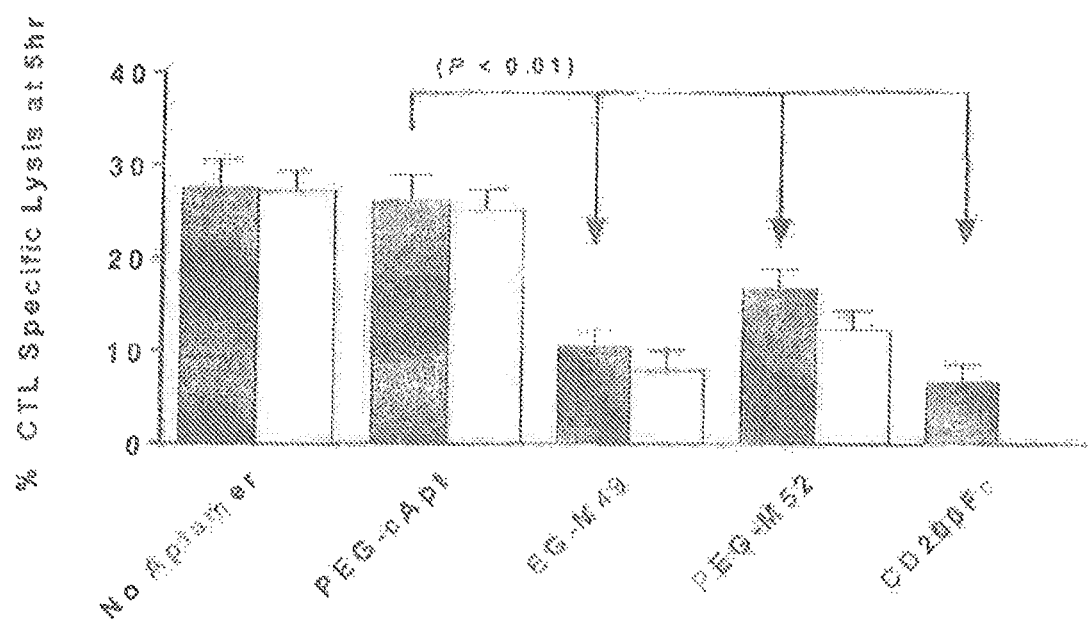
Figure 6A:
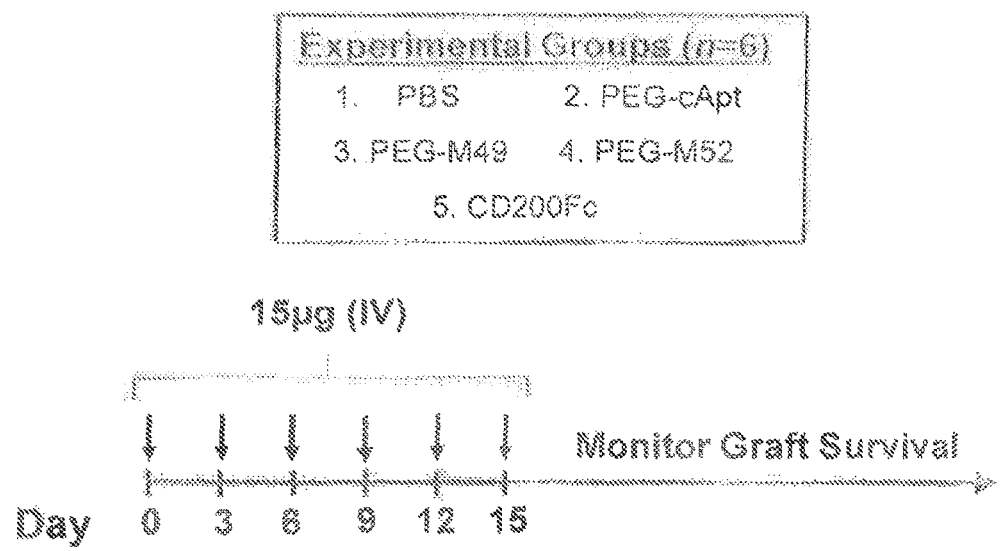
FIGS. 6A and 6B show PEG-M49 and PEG-M52 prolong survival of transplanted murine skin grafts.
Figure 6B:
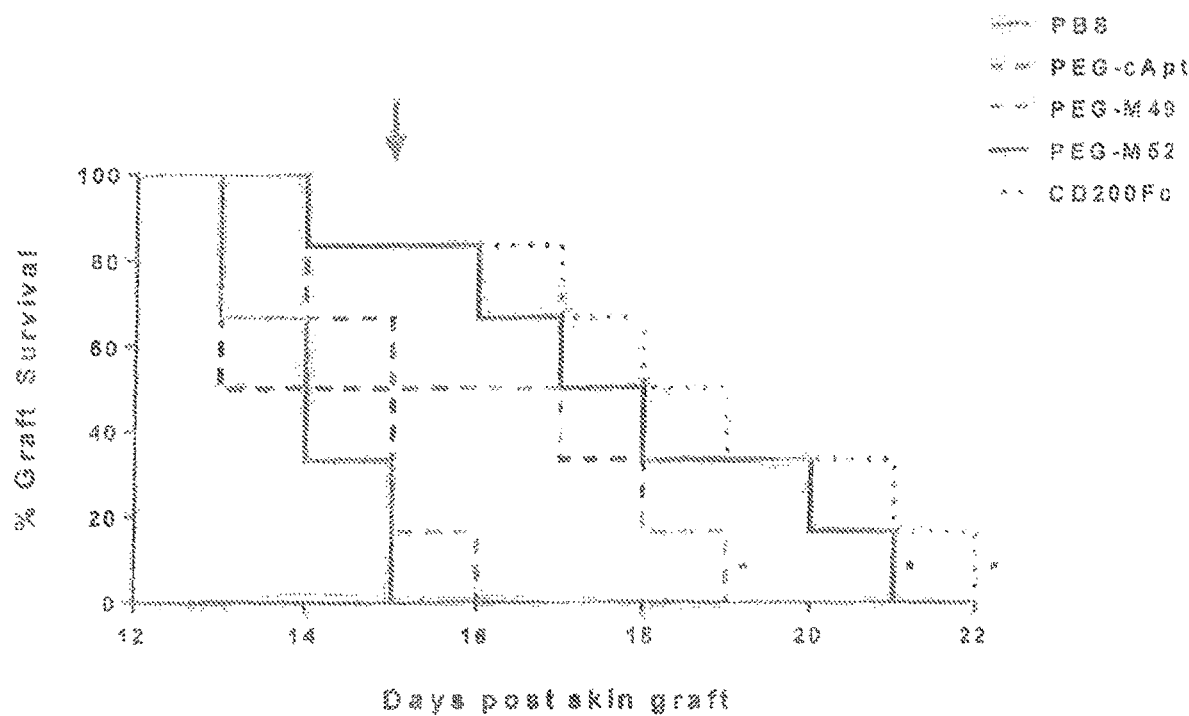
Figure 7A:
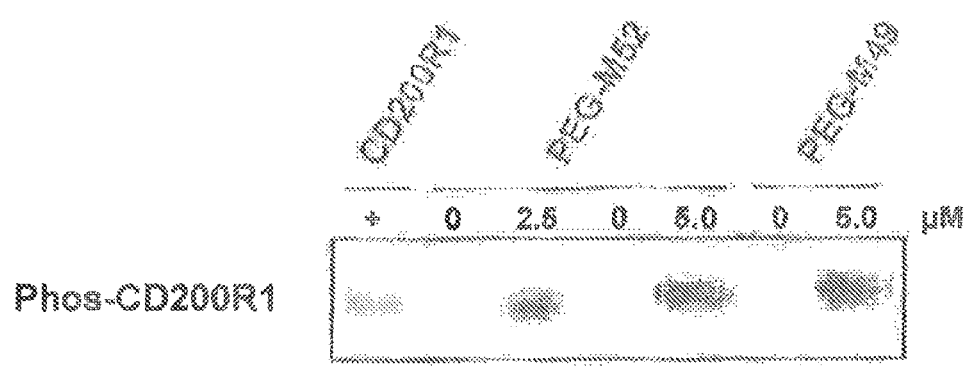
FIGS. 7A and 7B show PEG-M49 and PEG-M52 but not PEG-cApt stimulate phosphorylation of the C-terminal tail of CD200R1. HEK293 expressing CD200R1 cells were incubated with indicated concentrations of PEG-M49, PEG-M52, PEG-cApt, or CD200 positive cell supernatant for 30 minutes. CD200R1 was immunoprecipitated and detected on western blot with an antibody specific to phosphorylated CD200R1 C-terminal tail. Phosphorylation was detected at all concentrations of PEG-M49 or M52 (FIG. 7A and FIG. 7B) but not with PEG-cApt (FIG. 7B). (+) indicates addition of CD200+ supernatant, (−) indicates media alone. Shown is a representative from two independent experiments.
Figure 7B:
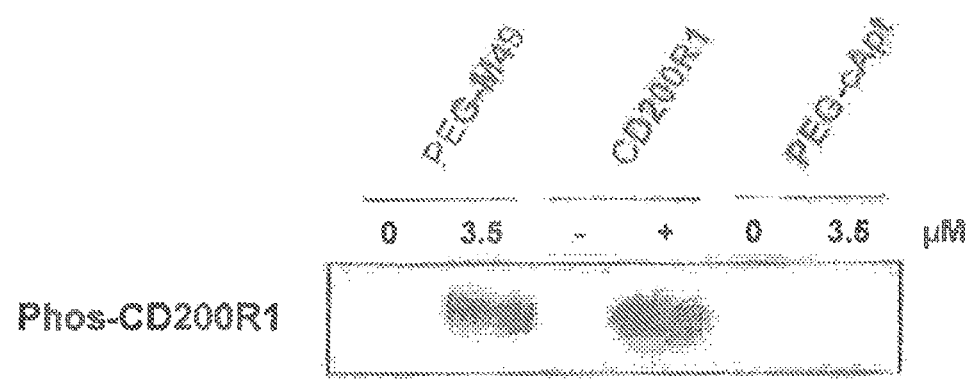

The PEGylated aptamers PEG-M49, PEG-M52, and PEG-cApt were compared to unconjugated aptamers for their capability to suppress CTL induction in allogeneic-MLC. Both PEG-M49 and PEG-M52 suppressed CTL induction to a greater extent than M49 and M52 (FIG. 4A), confirming that PEGylation did not disrupt the structure and function of these aptamers.

Example 4: Detection of CD200R1 Phosphorylation

Intracellular phosphorylation of CD200R1 in response to PEG-M49, PEG-M52, and PEG-cApt was detected using a rabbit polyclonal antibody specific to the phosphorylated cytoplasmic tail of CD200R1. HEK-293 cells stably expressing CD200R1 were serum starved in OptiMEM media (Life Technologies) for 3 hrs followed by incubation for 30 min with 2.5 μM PEG-M49, PEG-M52, PEG-cApt, or a CD200 positive cell lysate (positive control) in OptiMEM. Cells were washed in PBS, lysed in RIPA buffer with protease inhibitor, and CD200R1 immunoprecipitated using an anti-CD200R1 (clone 2A10) monoclonal antibody (overnight 4° C.) and Protein G agarose beads (Pierce). The phosphorylated form of CD200R1 was detected by western blot using the rabbit polyclonal antibody (1:1000 dilution) and anti-rabbit HRP (1:15,000 dilution).

The immediate signalling event following CD200: CD200R1 ligation is the phosphorylation of the tyrosine residue in the NPXY motif on the C-terminal cytoplasmic tail of CD200R1. The phosphorylated NPXY motif interacts with adaptor proteins thereby transducing immune inhibitory signalling. To confirm that the suppression of CTL induction observed in our allo-MLC assays was indeed a consequence of aptamer-induced CD200R1 signalling, we verified whether PEG-M49 and PEG-M52 could induce the phosphorylation of this motif. HEK-293 cells were stably transfected to express murine CD200R1 (FIG. 4B) and treated with aptamers PEG-M49 and PEG-M52. The phosphorylation of CD200R1 was detected using a phosphospecific antibody. Both PEG-M49 and PEG-M52 induced the rapid phosphorylation of the C-terminal tail of CD200R1 (FIG. 4C). There was no detectable signal from medium alone or PEG-cApt (FIG. 7) confirming that the identified aptamers signal through CD200R1 in a similar manner to CD200.

Example 5: Activity of PEGylated Aptamers In-Vivo

To stimulate an immune response C57BL/6 mice received BALB/c skin allografts (Day 0) followed by five tail vein injections of 15 μg PEG-M49, PEG-M52, PEG-cApt, or CD200Fc dissolved in 0.3 mL PBS, pH 7.4 every 72 hours over 12 days in combination with low dose (0.5 mg/kg) rapamycin administered intraperitoneally every 48 hours (shown schematically in FIG. 5A). On day 14, mice were sacrificed and splenocytes used as responder cells in 5 day ex-vivo allo-MLC with or without further aptamer addition in vitro.

CTL induction was significantly suppressed by treating animals with PEG-M49, PEG-M52, or CD200Fc alone but not with PEG-cApt ($P<0.01$) (Figure SB, grey bars). Exposure of circulating lymphocytes to PEG-M49 and PEG-M52 both in-vivo and after their recovery (in-vitro) did not significantly improve the suppression of CTL induction as compared to in-vivo alone (FIG. 5B). This finding suggests that the administration of PEGylated CD200R1 agonistic aptamers is sufficient to down regulate immune responses in-vivo and that such aptamers may serve as anti-inflammatory agents for diseases in which CD200:CD200R1 signalling is implicated.

Example 6: Allogeneic Skin Graft Transplantation

PEG-M49 and PEG-M52 were evaluated for their capability to prolong survival of allogeneic murine skin grafts. C57BL/6 mice (n=6) received BALB/c skin allografts (Day 0) prior to receiving 6 tail vein injections of 15 μg PEG-M49, PEG-M52, PEG-cApt or CD200Fc in 72 hr intervals over 15 days in combination with low dose (0.5 mg/kg) rapamycin administered intraperitoneally every 48 hrs. Graft survival was monitored daily by a blinded investigator.

Rapamycin at this dosage has been shown to have no effect on graft survival when administered alone. Treatment with PEG-M49 and PEG-M52 significantly extended allograft survival as compared to PBS or PEG-cApt groups (FIG. 6B) ($P<0.05$, Mantel-Cox Test). Interestingly, at the time of last injection (Day 15) only 16% of mice receiving PEG-M49 or PEG-M52 had rejected the allografts. After this time point, differences between CD200Fc and PEGylated aptamers may be linked to differing pharmacokinetic profiles as the circulatory half-life of PEGylated aptamers and therefore their bioavailability may differ from the protein CD200Fc.

Example 7: Cross Species CD200R1 Agonistic Aptamers

The existing enriched libraries from SELEX to human and mouse CD200R1 were deep sequenced using IonTorrent and compared to each other to identify overlapping sequences. These sequences were synthesized and screened for CD200R1 agonistic activity (suppression of CTL in allo-MLC) with cells of both human and mouse origin. The identified agonists termed CCS13 and CCS8 (SEQ ID NOs.: 3 and 16, respectively, see Table 1, above) were PEGylated and activity verified by human and mouse allo-MLC. To evaluate in-vivo immunosuppression C57BL/6 mice received BALB/c allografts (Day 0) and were treated with 15 ug PEGylated aptamers or CD200.Fc in combination (72 hrs, i.v) with low dose rapamycin (0.5 mg/kg, 36 hrs, i.p.). Immune responses were monitored at Day 15 by ex-vivo allo-MLC. Lastly therapeutic potential was evaluated by monitoring the capability of PEG-CCS13 and PEG-CCS8 to prolong survival of the C57BL/6 allografts using the same treatment regimen described above to a total of 15 days. Graft survival was monitored by a blinded investigator.

Aptamers CCS13 and CCS8 induced potent suppression of CTL induction (<50% specific lysis) in both human (FIG. 8B) and mouse allo-MLC (FIG. 8C). CCS13 and CCS8 were

Figure 9:
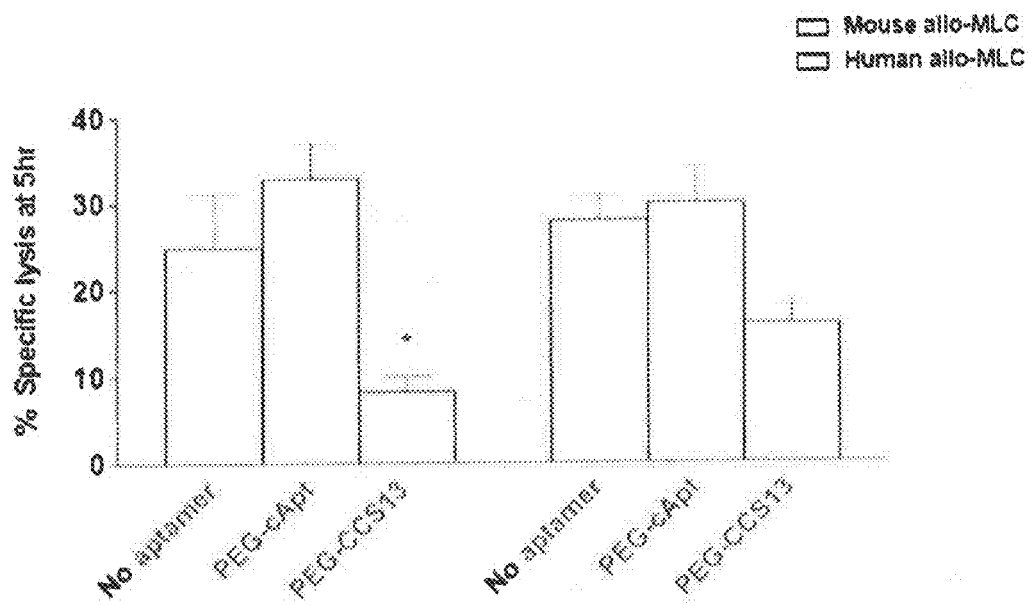
FIG. 9 shows conjugation of 20 kDa PEG to the 5' terminus of CCS.13 does not inhibit functional activity. Monofunctional Polyethylene glycol (PEG) was conjugated to a 5' amine modified aptamer with a C6 spacer overnight. Full length conjugated aptamers were purified using SEC-FPLC with a Superdex-75 column. PEG-CCS.13 along with a scrambled control sequence (PEG-cApt) was added at 3 ug/mL to 5 day human and mouse allogenic MLC to monitor suppression of CTL induction. CTLs were assayed by monitoring $^{51}$Cr release from loaded target cells at a 30:1 effector to target ratio in 5 hours. PEG-CCS13, but not PEG-cApt significantly (*P<0.05) suppressed CTL induction in human and mouse allogenic MLC.
Figure 10A:
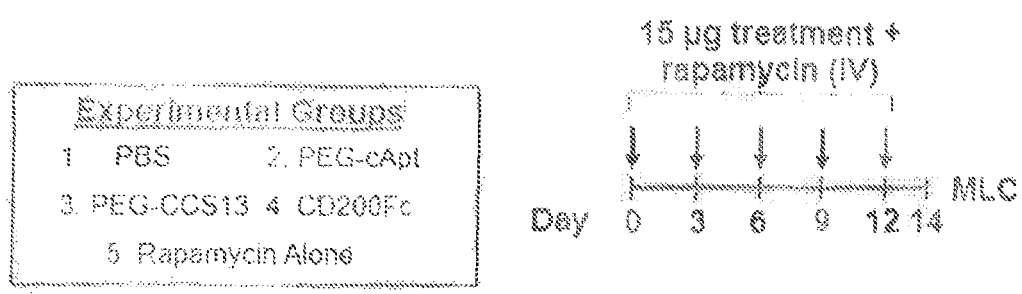
FIGS. 10A and 10B show PEG-CCS.13 functions in-vivo.
Figure 10B:
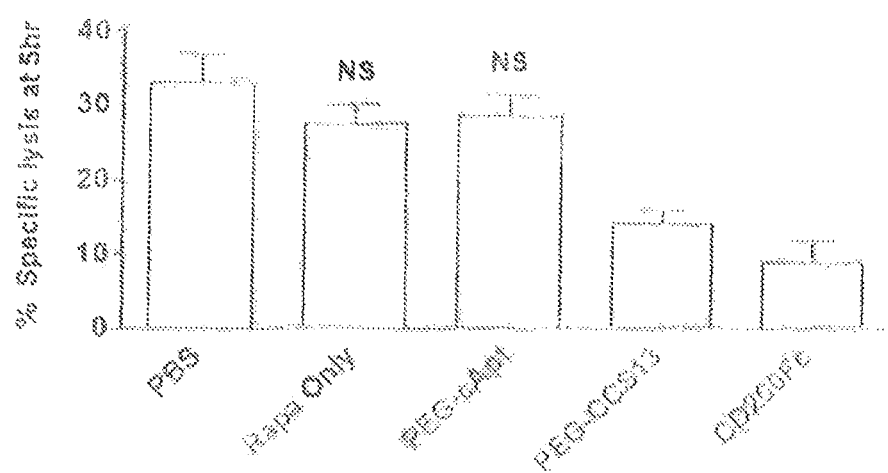
Figure 11A:
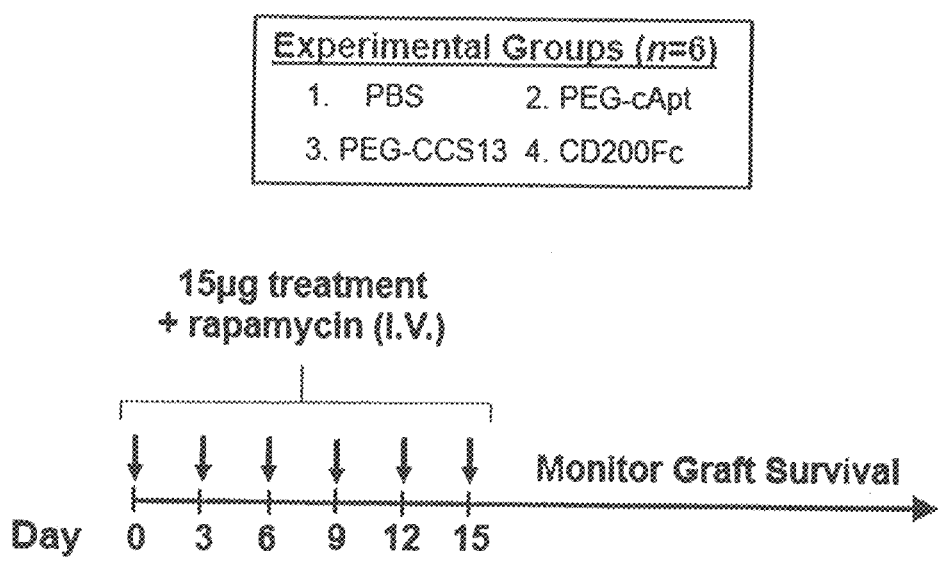
FIGS. 11A and 11B show PEG-CCS.13 but not PEG-cApt prolong survival of transplanted murine skin grafts.
Figure 11B:
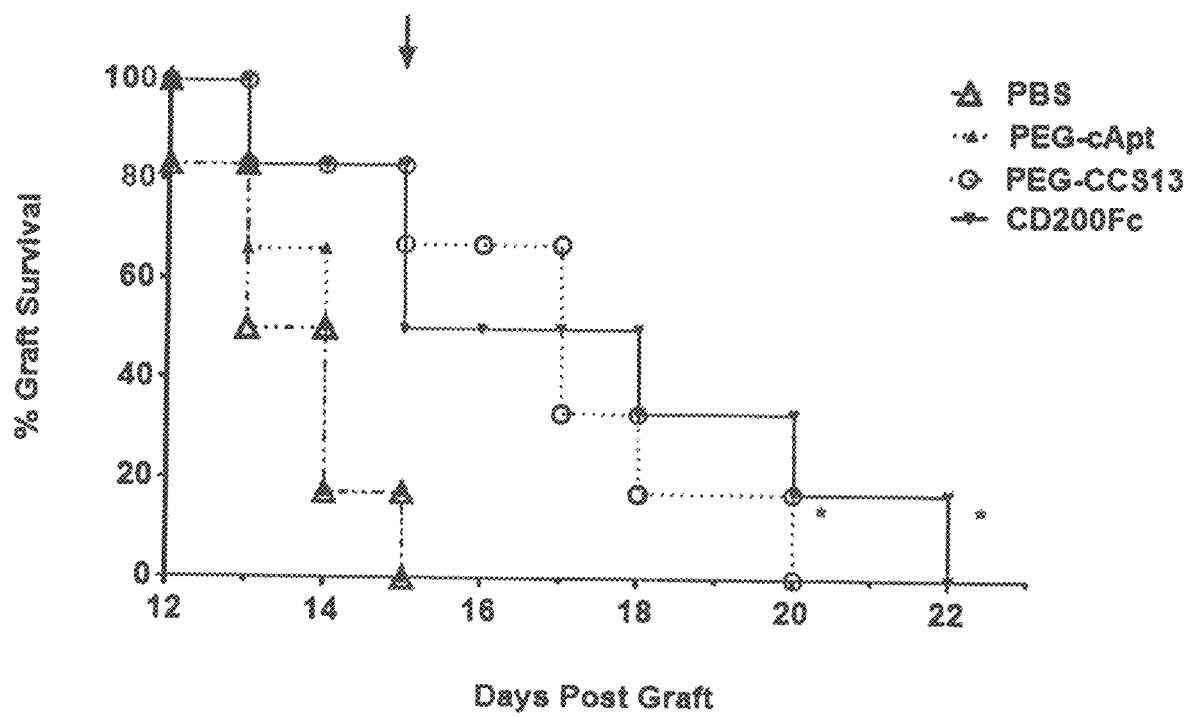

PEGylated and found to retain activity in 5-day in both human and mouse allo-MLC (FIG. 9). In-vivo administration of PEG-CCS8 and PEG-CCS13 significantly suppressed immune activity as measured by ex-vivo allo-MLC. (FIG. 10). Finally, PEG-CCS8 and PEG-CCS13 were found to significantly prolong allograft survival (FIG. 11).

Thus the aptamers CCS8 and CCS13 potently induced immunosuppression in both human and mouse allo-MLC. Furthermore PEGylated CCS13 and CCS8 retained this ability and functioned in-vivo to suppress immune response and prolong allograft survival.

Example 8: Detection of CD200R1 Phosphorylation

Figure 12:
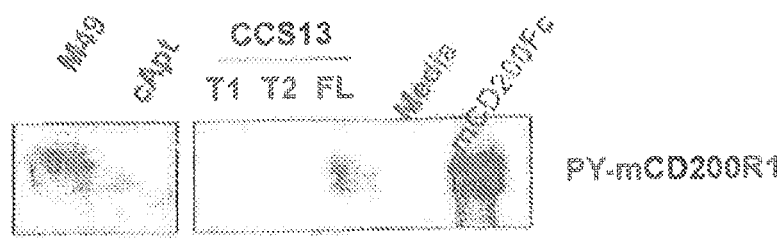
FIG. 12 shows CCS acts as a CD200R1 agonist by inducing phosphorylation of the CD200R1 cytoplasmic tail. To monitor aptamer induced phosphorylation of the CD200R1 cytoplasmic tail HEK293 cells transfected to stably express mouse CD200R1 were incubated with a positive control CD200R1 agonistic aptamer M49 (1.5 μM), a negative control aptamer cApt (3 μM), or full length (FL) or truncated versions (T1, T2) of the CD200R1 cross species aptamer CCS13 (all 3 μM). After a thirty minute incubate the cells were subsequently lysed and phosphorylation of the CD200R tail detected by western blot using an antibody specific to mouse phosphorylated-CD200R1 cytoplasmic tail. Treatment with CD200Fc (3.3 μM) or media alone were used as additional positive and negative controls respectively. Notably, full-length CCS13 but not its truncated versions were capable of inducing phosphorylation of the CD200R1.

Intracellular phosphorylation of CD200R1 in response to M49, as well as full length and truncated versions of CCS13 was detected using a rabbit polyclonal antibody specific to the phosphorylated cytoplasmic tail of CD200R1. HEK-293 cells stably expressing murine CD200R1 were serum-starved in OptiMEM (Life Technologies, Burlington, Canada) medium for 3 hrs and subsequently incubated for 30 min in OptiMEM medium containing either M49 (1.5 µM), negative control aptamer cApt (3 µM), CD200Fc (3.5 µM), or full length (FL) or truncated (T1, T2) versions of CCS13 (3 µM). Cells were washed with PBS and lysed in RIPA buffer (150 mM NaCl, 1.0% Igepal, 0.5% sodium deoxycholate, 0.1% SDS, and 50 mM Tris, pH 8.0) containing 50 mM NaF, 1 mM Na3VO4, and protease inhibitors. Phosphorylated and unphosphorylated forms of CD200R1 were recovered by immunoprecipitation using an anti-CD200R1 (clone 2A10) monoclonal antibody (overnight 4° C.) and Protein G agarose beads (Pierce). The phosphorylated form of CD200R1 was detected by western blot using the rabbit polyclonal antibody (1:1000 dilution) and anti-rabbit HRP (1:15.000 dilution) (FIG. 12). Full-length CCS13 but not its truncated versions were capable of inducing phosphorylation of the CD200R1.

Example 9: Treatment of Asthma with an Aerosolized, Nasally or Orally Inhaled Aptamer Methods of administering small molecules via an intranasal route, or via nasal or oral inhalation, are known. For example, a saline-based solution comprising the active small molecule can be administered as a mist; dry powder can be administered via a known dry powder inhaler.

In certain embodiments, administration of an effective amount of a CD200R1 agonist on its own, for example, an aptamer, such as a PEGylated aptamer (e.g., PEG-CCS13), is effective in treating asthma. In a particular embodiment, a solution of an effective amount of PEG-CCS13 is prepared using standard inhalation carriers, such as a saline mist, which can be administered intranasally or via nasal or oral inhalation for the treatment of asthma. Alternatively, a dry powder form of PEG-CCS13 is administered by a known dry powder inhaler.

In an alternative embodiment, PEG-CCS13 is added to an already known and existing treatment for asthma, such as a corticosteroid. It is expected that such a combination therapy may be particularly effective in treating asthma, for example, by having improved efficacy or a synergistic effect over administration of a corticosteroid alone, since a corticosteroid has a different and distinct mechanism of action than PEG-CCS13.

In another embodiment, a single dose of PEG-CCS13, provided intranasally, produces significant alleviation of asthma symptoms in an individual with asthma.

In yet another embodiment, a CD200R1 agonist, for example CCS13, conjugated to one or more active ingredients of known asthma medicines, provides an increase in the effectiveness of such medicines, by targeting those medicines to an appropriate location for improved effect.

The invention claimed is:

1. A method of treating asthma, comprising administering to a subject in need thereof an effective amount of an aptamer or oligonucleotide that binds to a CD200R1 target, wherein the aptamer or oligonucleotide is selected from the group consisting of CCS13 (SEQ ID NO:3), CCS8 (SEQ ID NO:16), TCCS8 (SEQ ID NO: 15), and TCCS13 (SEQ ID NO:6).

2. The method of claim 1, wherein the aptamer or oligonucleotide comprises at least one chemical modification.

3. The method of claim 2, wherein the modification is incorporation of a modified nucleotide.

4. The method of claim 2, wherein the modification is pegylation.

5. The method of claim 4, wherein the pegylation is a linear polymer of polyethylene glycol.

6. The method of claim 2, wherein the modification is 3' and 5' capping.

7. The method of claim 2, wherein the modification is conjugation to a high molecular weight, non-immunogenic compound; conjugation to a lipophilic compound; or conjugation to another oligonucleotide.

8. The method of claim 7, wherein the another oligonucleotide is an siRNA, an antisense oligonucleotide, a ribozyme, or a DNA/RNA chimera.

9. The method of claim 1, wherein the aptamer or oligonucleotide is conjugated or otherwise associated with a cytotoxic agent.

10. The method of claim 1, wherein the aptamer or oligonucleotide is an aptamer- or oligonucleotide-drug conjugate comprising the aptamer or oligonucleotide and a cytotoxic drug.

11. The method of claim 1, wherein the aptamer or oligonucleotide is an aptamer- or oligonucleotide-protein conjugate comprising the aptamer or oligonucleotide and a therapeutic protein.

12. The method of claim 1, wherein the aptamer or oligonucleotide is an aptamer- or oligonucleotide-radionuclide conjugate comprising the aptamer or oligonucleotide and a radionuclide.

13. The method of claim 1, wherein the aptamer or oligonucleotide is an aptamer- or oligonucleotide-metal chelator conjugate comprising the aptamer or oligonucleotide and a metal chelator.

14. The method of claim 1, wherein the aptamer or oligonucleotide is an aptamer- or oligonucleotide-nanostructure conjugate comprising the aptamer or oligonucleotide and a nanostructure.

15. The method of claim 1, wherein the aptamer or oligonucleotide is an aptamer- or oligonucleotide-chromophore conjugate comprising the aptamer or oligonucleotide and a chromophore.

16. The method of claim 1, wherein the aptamer or oligonucleotide is a pegylated CCS13 (SEQ ID NO: 3).

17. A pharmaceutical composition for the treatment of asthma comprising an aptamer or oligonucleotide selected from the group consisting of CCS13 (SEQ ID NO:3), CCS8 (SEQ ID NO:16), TCCS8 (SEQ ID NO: 15), and TCCS13 (SEQ ID NO:6) and a therapeutically acceptable carrier.

18. The pharmaceutical composition of claim 17 wherein the aptamer or oligonucleotide is pegylated.

19. The pharmaceutical composition of claim 18 wherein the aptamer or oligonucleotide is a pegylated CCS13 (SEQ ID NO: 3).

* * * * *